United States Patent [19]

Kelman et al.

[11] Patent Number: 4,969,912
[45] Date of Patent: Nov. 13, 1990

[54] HUMAN COLLAGEN PROCESSING AND AUTOIMPLANT USE

[76] Inventors: Charles D. Kelman, 269 Grand Central Pkwy., Floral Park, N.Y. 11005; Dale P. DeVore, 3 Warwick Dr., Chelmsford, Mass. 01824

[21] Appl. No.: 157,638

[22] Filed: Feb. 18, 1988

[51] Int. Cl.$^5$ .............................................. A61F 2/14
[52] U.S. Cl. ...................................... 623/66; 604/51; 128/DIG. 8; 8/94.11; 8/94.18; 623/4
[58] Field of Search ....................... 623/66, 11, 1, 6, 4, 623/5; 128/DIG. 8; 604/51; 8/94.11, 94.15, 94.18; 600/36

[56] References Cited

U.S. PATENT DOCUMENTS

| | | |
|---|---|---|
| 3,055,790 | 9/1962 | de la Burde et al. |
| 3,866,609 | 2/1975 | Sparks ................. 623/66 X |
| 3,949,073 | 4/1976 | Daniels et al. |
| 3,968,567 | 7/1976 | Nevins ................. 623/66 X |
| 4,164,559 | 8/1979 | Miyata et al. |
| 4,223,984 | 9/1980 | Miyata et al. |
| 4,260,228 | 4/1981 | Miyata . |
| 4,264,155 | 4/1984 | Miyata . |
| 4,381,007 | 4/1983 | Doss . |
| 4,383,832 | 5/1983 | Fraefel et al. ............ 8/94.11 |
| 4,505,855 | 3/1985 | Bruns et al. |
| 4,511,653 | 4/1985 | Play et al. |
| 4,544,638 | 10/1985 | Siegel . |
| 4,557,764 | 12/1985 | Chu . |
| 4,563,779 | 1/1986 | Kelman . |
| 4,581,030 | 4/1986 | Bruns et al. |
| 4,582,640 | 4/1986 | Smestad et al. ......... 128/DIG. 8 X |
| 4,676,790 | 6/1987 | Kern . |
| 4,695,281 | 9/1987 | Miyata et al. ............ 623/11 |

FOREIGN PATENT DOCUMENTS

| | | |
|---|---|---|
| 0214853 | 3/1987 | European Pat. Off. |
| 1015284 | 12/1965 | United Kingdom . |
| 2086724 | 5/1982 | United Kingdom . |

OTHER PUBLICATIONS

DeVore et al. "Viscoelastic Collagen For Use In Opthalmic Surgery", 1st Atlantic Congress, The Future Of Collgen Lyon, France, Sep. 10-12, 1985, Conferences, Tome II pp. 253-256.
Shakespeare et al., The Lancet, Apr. 12, 1980, pp. 795-796.
Oliver et al., British Journal of Plastic Surgery, 30:88-95, 1977.
Oliver et al., Biomaterials, vol. 3, 38-40, Jan. 1982.
Pruett, Arch. Ophthalmology, 88:540-543, 1972.
Stenzel et al., Science, 164:1282-1983, 1969.
Dunn et al., Science, 157:1329-1330, 1967.
Kawakami, Excerpta Med Int., Congress Series, 2:1432-1434, 1975.
Fijimore, Biochemistry, 5:1034-1040, 1966.
Miyata et al., Biochim. Biophys. Acta, 229:672-680, 1971.

Primary Examiner—Alan W. Cannon
Attorney, Agent, or Firm—Darby & Darby

[57] ABSTRACT

Production of a chemically modified, crosslinkable, telopeptide-containing, naturally crosslinked, solubilized collagen from tissue obtained from a sole human donor, for implanting in the same donor, by chemically modifying the tissue, e.g. by acylation and/or esterification, to form an autoimplantable, crosslinkable, telopeptide-containing naturally crosslinked, collagen, product, as a completely solubilized collagen solution, optionally of high index of refraction for correcting sight, or as a partially solubilized collagen suspension; and use of the product for altering the condition of in situ tissue of the same human donor by autoimplantation, such as by crosslinking the product to form an implant device, by placing an effective amount of the product at the tissue site and crosslinking the product in situ, or by partially crosslinking the product and placing an effective amount thereof at the tissue site and optionally further crosslinking the product in situ.

11 Claims, 1 Drawing Sheet

HUMAN COLLAGEN PROCESSING AND AUTOIMPLANT USE

FIELD AND BACKGROUND OF THE INVENTION

The present invention relates to human collagen processing and autoimplant use, and more particularly to a chemically modified, crosslinkable, telopeptide-containing, naturally crosslinked, solubilized collagenous substance obtained directly from intact human tissue from a sole human donor, for implanting in various forms in the same said donor, and to the process for making such product.

In general, the collagens are ubiquitous proteins found throughout the animal kingdom. All known collagens are rod-like structures. Interstitial collagens are 3,000 Å long and 15 Å in diameter. The conformation and most of the properties of native collagen are determined by the triple helix domain which composes more than 95% of the molecule. This domain consists of three chains (alpha chains), each containing approximately 1,000 amino acids, wrapped in rope like fashion to form a tight, triple helix structure. The triple helix is wound in such a way that peptide bonds linking adjacent amino acids are buried within the interior of the molecule.

In native molecules the triple helix retains its resistance to attack by general proteases such as pepsin. Collagen molecules (tropocollagen) found in the extracellular matrices also contain short (e.g. about 16–25 peptide unit) non-helical extension peptides, called "telopeptides", at both the NH— and COOH— terminal ends of each alpha chain. These telopeptides are susceptible to proteolytic degradation and removal under conditions in which the triple helical body is left intact (as atelopeptide collagen).

Native collagen is generally present in connective tissue as telopeptide-containing tropocollagen molecules in side by side packed condition in the form of fibrils, with each longitudinal course composed of slightly longitudinally spaced apart molecules in end to end disposition, staggered longitudinally relative to the next successive laterally adjacent longitudinal course, thereby resulting in holes between facing end regions of successive molecules in a given longitudinal course and bounded by the staggered sides of the molecules in the parallel longitudinal courses laterally adjacent thereto.

These fibrils, e.g. of about 5 to 7 parallel courses packed together, in turn are arranged in bundles to form fibers which, along with the cells themselves, exist in the tissue in a ground substance of noncollagenous material as matrix. In bone, such holes in the staggered packing arrangement may contain mineral substances such as calcium phosphates.

In this native form, adjacent telopeptide-containing end moieties of a given molecule in a fibril are crosslinked to helical regions of adjacent molecules. The helical or central regions of the polypeptide chains or strands of a given molecule are crosslinked to each other (intramolecular crosslinks) to form a triple helix. The telopeptide and helical regions of neighboring molecules are likewise crosslinked to strands of neighboring molecules (intermolecular crosslinks), thereby forming hydrogen crosslinked or bonded and covalently crosslinked or condensed insoluble collagen. Where few, if any, stabilized reducible, crosslinks are present, the molecules in the fibril are considered soluble, i.e. the collagen is solubilized in aqueous salts, acids and bases, leaving unsolubilized the highly stabilized, crosslinked insoluble collagen.

The most common type of collagen isolated from many adult connective tissues such as skin, bone, tendon, and cornea is type I collagen. Each type I molecule is composed of two alpha 1 (I) chains and one alpha 2 (I) chain. The entire molecule is abbreviated alpha 1 $(I)_2$ alpha 2 (I).

Collagen is probably the first biomaterial ever used by man for surgical purposes. Dried intestine, predominantly composed of collagen, was used by Egyptian surgeons as a surgical suture as far back as 3750 B.C.

Numerous properties of collagen favor its use as a biomaterial; see Biomaterials in Reconstructive Surgery, Ch. 11, Simpson, "Collagen as a biomaterial", pp. 109–117, The C. V. Mosby Co., 1983. It is absorbed at a rate that can be controlled by the degree of chemical treatment to which it is subjected. One can thus design collagen products which, on animal implantation, will be completely absorbed in a few days or months. One can chemically treat animal source collagen so that it becomes essentially totally non-absorbable while still retaining its hydrophilic character and its good tissue response.

Collagen has a high order of tensile strength and low extensibility, and can be reconstituted into membranes, sheets, tubes, sponges, or continuous length fibers. As a membrane, it is semi-permeable and a good support for cell growth. It has drug binding properties and is, for all practical purposes, immunologically inert.

The chemical and physical characteristics of collagen, its widespread distribution in many different tissues, and the ability to extract and purify and then reconstitute collagen into many physical forms would appear to make the natural polymer an ideal biomaterial. Many applications for collagen compositions have been suggested:

(A) solution form collagen applications: plasma expander, and drug delivery vehicle;

(B) gel form collagen applications: vitreous body additive, and cosmeticum;

(C) flour form collagen application: hemostatic agent;

(D) fiber form collagen applications: suture material, weaving of blood vessels, and valve prosthesis;

(E) film or membrane form collagen applications: corneal replacement, hemodialysis, artificial kidneys, wound dressing, hernia repair, and patches (aneurysm);

(F) sponge form collagen applications: wound dressing, bone-cartilage substitute, surgical tampon, and vaginal contraceptive; and (G) tubing form collagen applications: vessel prosthesis, and reconstructive surgery of hollow organs.

However, until recently, the only clinically available collagen device was animal source suture material from intestines and from reconstituted collagen. Today there are at least two additional clinical devices composed of animal source collagen, to wit, hemostatic agents, and the Zyderm Collagen Implant (Collagen Corporation) or ZCI; see Grosh et al, J. Am. Acad. Dermatol., 13:792–798, 1985.

Pertinent prior art describes methods of chemically modifying soluble collagen by reactions with either amine or carboxyl groups on the collagen molecule. These methods render the solubilized collagen soluble at physiological pH. Collagen is generally solubilized by treatment with acids, including organic acids such as acetic acid and citric acid, and inorganic acids such as hydrochloric acid, and especially by proteolytic enzyme treatment. The solubilized collagens contain few, if any, intermolecular crosslinks and remain soluble under acidic conditions and spontaneously form fibers at physiological pH.

Modification of either amine or carboxylic moieties changes the pK of the molecule. For example, by modification with succinic anhydride, the pK changes from 7.0 to 4.3. The succinylated collagen will remain soluble at pH 7.0 and will form fibers at pH 4.3.

These overall methods, however, generally removed the telopeptide groups.

SUMMARY OF THE INVENTION

It is among the objects of this invention to produce a chemically modified, crosslinkable, telopeptide-containing, naturally crosslinked, solubilized collagenous substance obtained directly from intact human tissue from a sole donor, for altering the condition of in situ tissue of the same donor, e.g. for augmenting soft tissue, by autoimplantation.

Briefly, this invention concerns the processing of collagens from a biopsy or other specimen of human skin or other human tissue (e.g. skin or bone for Type I fibrous collagen, or cartilage for Type II collagen), for use as a biological autoimplant in the same tissue donor alone.

Such autoimplants contemplate two major categories, i.e. intradermal implants to augment soft connective tissue or correct skin defects such as wrinkles and scars; and ophthalmic implants, e.g. intralamellar, corneal overlay coating or reshaping, vitreous, and other implants, in refractive surgery to correct refractive errors of vision, change corneal curvature, replace vitreous humor, and the like; as well as other categories of implants such as those used in other surgical procedures where there is a need to replace, augment or otherwise change the condition of connective tissue, e.g. in the form of matrix material for skin grafts, matrix substances or components for cell seeding and grafting, material matrix for tissue "putty" or filler, and the like.

This invention also concerns novel processing techniques for extraction from intact human tissue of insoluble, naturally crosslinked, native, telopeptide-containing collagen by reacting such collagen, obtained from the donor patient alone, with chemical reagents that render the insoluble collagen more soluble in physiological aqueous solutions, significantly without acidic or alkaline hydrolysis or enzymatic degradation, and such that the extracted or solubilized telopeptide-containing, naturally crosslinked, collagens can be further purified and then chemically or physically treated to provide fibrous structures, flour like particles, gels, sponges, clear and colorless solutions, or suspensions, or the like for autoimplanting in the same human donor.

In intact human tissue, the telopeptide-containing triple helix collagen units of the staggered packed array of tropocollagen molecules of the fibrils, are in highly crosslinked, insoluble condition. The helical or central regions are high in glycine, proline and hydroxyproline amino acid residues, and the telopeptide or end appendage regions contain aromatic residues (tyrosine) and do not exhibit the glycine-X-Y triplet found in the helical region.

The individual helical chains or strands of the triple helix molecules are arranged in side by side intramolecularly and/or intermolecularly crosslinked disposition along the corresponding collagen polypeptide backbone, such that the terminal amino group-containing site of each given strand is linked to its adjacent non-helical telopeptide end moiety, and the terminal carboxylic acid group-containing site of the same strand is linked to its adjacent non-helical telopeptide end moiety. The nonhelical regions are crosslinked, intramolecularly, with helical regions of adjacent molecules.

Heretofore, in normal processing to extract the collagen by solubilization, conditions were used which resulted in the severing of the helical strands from one another and/or the severing of the strands from their telopeptide units to form individual triple helix collagen strand subunits or atelopeptides. This normally rendered the resulting atelopeptide or solubilized collagen soluble at acidic pH and insoluble at neutral pH.

By way of the invention, the extraction and recovery of the collagen from the human tissue is carried out essentially without severing the triple helical strands from each other, or the telopeptide end moieties from the opposite ends of the helical regions of the individual strands. Thus, the original intact linking of the individual units along the polypeptide backbone, and the original intact natural crosslinking between adjacent helical strands and between adjacent non-helical telopeptide end units, are essentially preserved. Instead, the intact collagen is chemically modified to solubilize it at neutral or basic pH, and render it insoluble at acidic pH.

Unlike previously used acid soluble and enzyme digested forms of extracted and chemically modified atelopeptide collagen products, the telopeptide-containing, naturally crosslinked, collagen product of this invention is believed to be more compatible with the tissue environment of the same human donor, and more resistant to degradation, absorption, rejection, or other attack by in situ constituents of such donor, possibly because it is desirably made free from noncollagenous protein contaminates, and preferably also from lipid constituents, but more particularly because it preserves the telopeptide moieties and the natural crosslinks and chemically provides additional crosslinking sites.

No antigenic potential need be feared since the human tissue processing contemplated by this invention involves only autologous tissue, i.e. obtained from the very same person in whom the product is reimplanted, as opposed to heterologous tissue, i.e. obtained from another person than the one in whom the product is transplanted.

Hence, per this invention, due to the autologous nature of the human tissue, no antibody response or rejection is to be expected, whereas due to the contemplated chemical modifying and crosslinking of the product, the autoimplanted product will serve as a relatively more permanent implant material than previously known products.

Nevertheless, based on this specific autologous tissue distinction, over the known heterologous tissue use, this invention also broadly permits altering the condition of in situ tissue of a human donor by autoimplantation, using an autoimplantable or reimplantable, processed collagenous substance derived from intact tissue of the very same human donor alone, regardless of the means or process used to extract and chemically modify the tissue, and whether the processing is such that the completely or partially solubilized collagen still contains telopeptide moieties, as is preferred, or results in the less preferred formation of completely or partially solubilized atelopeptide collagen as in the past.

This is because a salient independent feature of this invention concerns the concept of autoimplantation of a collagenous substance product in a human donor which has been derived from intact tissue of that same donor alone, thus avoiding potential problems associated with antigenicity, rejection and the like of heterologous tissue transplants.

This invention thus provides forms of processed human tissue derived collagen serving as a long term, practical and relatively safe autoimplant product, e.g. permitting its production almost contemporaneously with its use in a given surgical procedure as a corneal, skin, coating, interconnecting layer, or the like implant at a surgical site. Of course, all such procedures are effected under sterile, antiseptic conditions using sterile materials.

BRIEF DESCRIPTION OF THE DRAWINGS

Other objects of this invention will become apparent from the within specification and accompanying drawings, in which.

DESCRIPTION OF THE PREFERRED EMBODIMENTS

According to one aspect of this invention, a process is provided for producing a chemically modified, crosslinkable, telopeptide-containing, naturally crosslinked, solubilized collagenous substance obtained directly from intact human tissue from a sole donor, for implanting in the same donor.

The process comprises desirably removing attendant noncollagenous protein contaminates from telopeptide collagen-containing intact tissue, which has been obtained from a sole human donor, to form essentially purified telopeptide collagen-containing tissue material, and extracting and chemically modifying the purified telopeptide collagen to form an autoimplantable, crosslinkable substance.

The contaminates may be removed by contacting the tissue with a substantially neutral liquid which is capable of solubilizing contaminates without solubilizing the collagen, or by utilizing specific enzymes to solubilize noncollagen tissue components. The contaminate-free telopeptide collagen is then extracted and chemically modified by reaction of the tissue directly with a chemical modifying agent.

In one embodiment, the chemical modifying agent is an amine reactive, especially acylating, agent, and the reaction is carried out in a solubilizing aqueous medium of substantially neutral to basic pH sufficiently to solubilize at least partially the telopeptide collagen in the aqueous medium, with the at least partially solubilized collagen thereafter being recovered and purified to form the autoimplantable telopeptide-containing collagenous substance as product.

In another embodiment, the chemical modifying agent is a carboxylic acid reactive, especially esterifying, agent, and the reaction is carried out in a solubilizing nonaqueous organic medium at acidic pH sufficiently to solubilize at least partially the telopeptide collagen therein, with the at least partially solubilized collagen thereafter being recovered and purified to form the autoimplantable telopeptide-containing collagenous substance as product.

Alternatively, the chemical modifying may include both the amine acylating and carboxylic acid esterifying steps.

The solubilized, chemically modified product comprises a backbone of telopeptide-containing collagen, derived from human tissue, having acylated amine groups and/or esterified carboxyl groups. More particularly, it comprises triple helix strands of telopeptide-containing collagen, derived from human tissue obtained from a sole donor, including polypeptide backbones having appended thereto by chemical modification, at least one of (a) acylated amine, and (b) esterified carboxyl, groups.

For preliminary removal of the noncollagenous protein contaminates, tissue homogenates may be prepared by blending the tissue in a tissue mill at a temperature of at most about room temperature sufficiently to grind, pulverize and disrupt the tissue material, for instance in contact with an aqueous saline solution of physiological pH, such as 0.9% NaCl of neutral pH, after which the liquid phase containing the solubilized contaminates may be separated off from the pulverized tissue material still containing the telopeptide collagen constituents as a solids phase or tissue powder.

The homogenate generally contains about 70% dry weight collagen and a remainder of debris and other constituents in the aqueous solution.

Favorably, the blending or homogenizing of the tissue is carried out by pulverizing the tissue in a frozen state, per cryopulverization technique, such as by freezing the tissue in liquid nitrogen and grinding the frozen tissue using a mortar and pestle or by way of a cryopulverization mill, whereby to increase the solubilization of the contaminates and reduce the overall processing time.

Preferably, the process also contemplates removing attendant lipid constituents from the collagen-containing tissue prior to the chemical modifying step and uses organic solvents to reduce bioburden levels inherent in the tissue to help reduce any bioburden from the tissue. For instance, the lipid removal step may be effected after the step of removing attendant noncollagenous protein contaminates from the tissue, so as to form essentially noncollagenous protein contaminate-free, as well as essentially lipid-free, telopeptide collagen-containing human tissue material, for the subsequent chemical modifying step.

The lipid removal step is thus effected in the initial stages of processing of the human tissue, and may comprise conventional treatment of the tissue, e.g. after mincing or pulverization, with a fat dissolving or lipophilic organic solvent system. The solids phase or tissue powder is mixed, for example, with an organic solvent such as ethanol or isopropanol, or with acetone, and preferably with 20 volumes of ethanol (95–98%), to extract the lipid components and any other organic solvent extractables from the collagenous material. The extracted powder is recovered by centrifugation, and washed, e.g. three times with 20 volumes of deionized water or other appropriate aqueous medium.

The solubilization of the telopeptide-containing collagen will occur at any reaction temperature between about 0°–45° C., but is preferably effected at about 20°–37° C., and especially at room temperature (about 25° C.), for convenience and for complete solubilization, if desired, in a reasonably short time.

For the amine modifying reaction, the noncollagenous protein contaminate-free, and lipid-free extracted, tissue powder is resuspended in aqueous medium. The suspension may be in any appropriate aqueous medium such as water, deionized water, balanced salt solution, saline solution, etc., preferably 0.9% isotonic saline solution.

Although the amine modifying reaction will proceed at a pH of 7 to 11, it is preferably effected at mildly basic pH to increase the reaction speed and reduce the processing time. The reaction is desirably effected at about pH 8.0-10.0, and especially at about pH 8.5-9.0.

The amine reactive modifying agent used as solubilizing agent may be an acylating agent, such as a carboxylic acid anhydride, e.g. succinic anhydride, glutaric anhydride, benzoic anhydride, 1,2,4,5-benzene tetracarboxylic acid dianhydride; carboxylic acid ester, e.g. monophenyl terephthalate, ethyl benzoate, alpha-naphthoic acid ethyl ester; carboxylic acid halide, e.g. succinic acid chloride; sulfonic acid, e.g. 1,3-benzene-disulfonic acid, aniline-2-sulfonic acid, 3-nitrobenzene-sulfonic acid, 2-formylbenzene-sulfonic acid, 4-aminonaphthalene-sulfonic acid; or sulfonic acid halide, e.g. 4,4'-biphenyl-disulfonyl chloride, benzene sulfonyl chloride; and mixtures thereof.

In general, the acylating agent may be an aliphatic or aromatic, mono-, di- or higher functional, carboxylic acid anhydride, ester or halide, or sulfonic acid or halide, such as a lower alkanoic, lower alkane-dioic or higher functional lower alkane carboxylic, or aryl mono-, di- or higher functional carboxylic (e.g. benzoic or naphthoic), acid anhydride, ester or halide, or lower alkyl, or aryl (e.g. phenyl or naphthyl), mono-, di- or higher functional sulfonic acid or halide, to provide the corresponding acyl (carbonyl or sulfonyl) moiety on the amine group, e.g. lower alkanoyl, aroyl (e.g. phenoyl or naphthoyl), alkyl sulfonyl, or aryl (e.g. phenyl or naphthyl) sulfonyl, substituted amino (amido or sulfonamido).

The acylating agent may be added directly as a solid material, e.g. powder, or dissolved in a suitable organic solvent such as acetone, N,N-dimethylformamide (DMF), ethanol, or methyl pyrrolidone.

The total quantity of acylating agent added depends on the extent of disruption, modifying and extracting of the telopeptide collagen desired. For instance, one addition at 150 mg agent per gram of wet tissue may not be sufficient to disperse and solubilize totally the collagen content of the tissue; as many as four such additions may be required.

The quantity required should generally satisfy the weight ratio of acylating agent to wet tissue of broadly 0.005-0.5:1, and preferably 0.05-0.1:1.

The reaction time for achieving complete solubilizing of the collagenous tissue may range from about 30 minutes to 2 hours. The time depends on the quantity of solubilizing agent, specific solubilizing agent used, rate of agitation or stirring, temperature, pH, and degree to which the tissue was initially pulverized or dispersed in the preliminary homogenization treatment.

For the carboxylic acid modifying reaction, the noncollagenous protein contaminate-free, and lipid-free extracted, tissue powder is desirably dried, e.g. in vacuo or by freeze drying, and combined with a carboxylic acid reactive esterifying agent in a nonaqueous organic medium at acidic pH, preferably no more than about pH 3.2, such as about pH 0.1-3.2.

The quantity required should generally satisfy the weight ratio of esterifying agent to dry tissue of broadly 1-30:1, preferably 1-20:1, and more preferably 5-20:1.

In particular, the medium is advantageously a large excess of the esterifying agent in the form of an acidified liquid, such as an acidified alcohol, especially an aliphatic alcohol, such as a water soluble lower alkanol, e.g. methanol and ethanol. The esterification reaction which forms the ester and water is favored by use of an excess of the alcohol to assure efficient formation of the ester product, in the presence of a catalytic amount of an acid such as 0.1N HCl as acidifying agent, e.g. providing a system pH of about 0.1-3.2.

The reaction is desirably effected under anhydrous conditions using dehydrated starting materials for optimum results, although acceptable results are still obtainable with starting materials which have not been dehydrated, e.g. using wet tissue powder.

In general, the esterifying agent may be an aliphatic or aromatic alcohol, such as a lower alkanol or an aryl alcohol (e.g. a phenol or a naphthol), to provide the corresponding aliphatic or aromatic, e.g. alkyl or aryl (e.g. phenyl or naphthyl), ester.

Where the esterifying agent is a solid at room temperature, it may be dissolved in a suitable nonaqueous organic solvent such as acetone, N,N-dimethylformamide (DMF), ethanol, or methyl pyrrolidone, as the organic medium.

The esterification reaction is conducted at the same temperature and for the same reaction time as the acylation reaction, for the same reasons, but since the esterifying agent is advantageously used in large excess as nonaqueous organic reaction medium, the esterifying agent amount will preferably be several times larger than that of the dry starting tissue, e.g. in a weight ratio thereto of 2-20:1, although the ratio may be 1-30:1, and preferably 1-20:1, in general, especially where the esterifying agent is a solid and an organic solvent is used as the reaction medium.

Where the tissue powder has already been solubilized by the amine modifying reaction, the recovered and purified acylated product may be dried, e.g. in vacuo or by freeze drying, and then combined with the acidified esterifying agent and reacted to form the corresponding acylated and esterified product. Alternatively, the tissue may first be subjected to the esterification step and the esterified solubilized product then subjected to the acylation step.

The reaction mechanism for solubilization of the collagen requires a free amine reactive group ($NH_3^+$) for the acylation step, or a free carboxyl reactive group ($COO^-$) for the esterification step. Typically, such free reactive groups are located in the tertiary position or at the terminal position (of the side chain) in the polypeptide structure. The two primary reactive groups on collagen molecules are (i) the epsilon amino group on lysine, and (ii) the carboxyl groups on aspartic acid and glutamic acid:

Lysine
pKb = 9.74

Aspartic Acid
pKa = 2.87

Glutamic Acid
pKa = 3.22

For instance, the $NH_3^+$ polar groups (cationic) will react with anhydrides, acid halides, sulfonyl halides and active esters such as monophenyl terephthalate. These agents will change the charge on the lysine amino group from positive (+) to negative (−), and the resulting collagenous structure will be more soluble at neutral pH.

Analogous changes from negative (−) to positive (+) occur upon esterifying the aspartic and glutamic acid $COO^-$ polar groups (anionic) with alcohols.

The reaction may be effected until the collagen is substantially completely solubilized in the medium, and the solubilized collagen recovered, purified and combined with aqueous liquid to form a telopeptide collagen solution as product.

In the case of the acylation reaction in aqueous medium at neutral to basic pH, the solubilized telopeptide-containing collagen may be rendered insoluble by acidifying the reaction medium to a pH of 3.5–5.0, and preferably to 4.0–4.5. The precipitate may then be recovered.

In the case of the esterification reaction in nonaqueous organic medium at acid pH, the solubilized telopeptide-containing collagen may be recovered by drying, e.g. in vacuo, or by mixing the acidified alcoholic solution with ethyl ether (e.g. 1:1 volume ratio) and then extracting the collagen from the organic mixture with water.

For specific ophthalmic applications, it is preferable that the modifying agent be capable of modifying the collagen to provide a solubilized collagen with a high index of refraction. This is most effective for correcting sight. The solubilized collagen is recovered, purified and combined with aqueous liquid to form a telopeptide collagen solution, of selective index of refraction for correcting sight, as product.

The agent used to achieve such selective index of refraction (nD) is suitably an amine modifying acylating agent which is capable of achieving complete solubilization of the collagen to provide a product that is essentially completely soluble at physiological pH conditions, such as aniline-2-sulfonic acid (nD=1.586), 3-nitrobenzene-sulfonic acid (nD=1.550), 2-formylbenzene-sulfonic acid (nD=1.544), 1,3-benzene-disulfonic acid, 1,2,4,5-benzene-tetracarboxylic acid dianhydride, or like reagents whose particular constituent reactive group or functional group exhibits a high index of refraction or imparts a resultant high index of refraction to the so modified collagenous substance.

Thus, such agent will generally possess an index of refraction of at least about nD 1.500, such as an index of refraction of from about nD 1.500 to about nD 1.600.

Alternatively, the reaction may be carried out until the collagen is only partially solubilized to provide a mixture of relatively larger fibrous particles and suspendable fine fibrous particles of unsolubilized telopeptide collagen in a homogeneous, e.g. gelatinous, mass of solubilized telopeptide collagen, and the suspendable fine particles and solubilized collagen recovered, purified and combined with aqueous liquid to form a fibrous telopeptide collagen suspension as product.

The product in each case may be formed into an injectable flowable mass, a putty like spreadable mass or filler, e.g. of film-forming solution or suspension product material, or finely divided distributable, e.g. dry powder, particles, and all forms of the product may be crosslinked, i.e. before and/or after autoimplantation.

Prior to implantation, each such product form is optionally partially crosslinked, i.e. insufficiently to form a shape retaining mass, yet for the injectable and putty like forms sufficiently for selective viscosity increase, and upon implantation such is optionally crosslinked in situ, or in the case of an implant device the product form is fully crosslinked before implantation.

Crosslinking may be effected, for instance, thermally, chemically with an isocyanate or aldehyde, such as glutaraldehyde, or by irradiation with gamma, or more preferably ultraviolet, rays. Ordinarily, crosslinking will be effected by a chemical crosslinking agent beforehand, or by ultraviolet light irradiation of the product in situ at the implantation site.

Understandably, use of heat or gamma irradiation is less preferred because these may adversely affect the integrity of the collagen, e.g. heat may cause denaturing of the collagen, and gamma irradiation may cause degradation, excessive polymerization, and/or undue yellowing of the collagen depending on the radiation dosage or intensity.

If desired, materials such as glycerol or glucose which retard collagen fibril formation, may be added to the injectable collagen preparation to stabilize the collagen.

The implant products include injectable flowable masses as vitreous humor implants, particle derived composite layer or sponge implants, and shape retaining coating and interconnecting layer implants as fiber, film, tubing, lens, and like structures.

In particular, the product may be formed into a mass of selective shape and size corresponding to an effective implant device, and thereafter crosslinked to produce such device.

It will be realized that ophthalmic autoimplants need to be essentially optically clear, considering their purpose in correcting sight, while soft tissue autoimplants, e.g. intradermal implants, need to be generally fibrillar or particulate so as to provide desired structural strength.

Hence, optically clear implant material is prepared by complete solubilization of the starting tissue. On the other hand, fibrillar or particulate implant material requires only partial solubilization of the starting tissue to fragment the starting tissue into a physical form of the product collagenous substance capable of being injected through a suitable size needle, e.g. a 25 to 30 gauge needle, without detriment to the form of the injectable mass or difficulty in achieving proper flow delivery to the implant site. Ordinarily, the particulate form of the collagenous substance will likely contain some solubilized form as well.

It has been found unexpectedly that the preparation of the high index of refraction solubilized collagenous material is achievable by using as chemical modifying agent a modifier, e.g. acylating agent, having a higher index of refraction than otherwise necessary for generally achieving complete solubilization of the collagenous substance. The solubilization specifically operates with this high index of refraction modifier or reagent so as to result in the production of a clear preparation having a higher index of refraction than otherwise obtained using a chemical modifying agent, e.g. acylating agent, in general.

This higher index of refraction clear preparation, or high index of refraction collagenous substance product, is considered to be eminently usable effectively to correct refractive errors in sight, especially in view of the fact that the higher the index of refraction, the thinner the film needed to correct the error, and thus the lesser the amount of starting tissue needed to be obtained from the human donor.

According to another aspect of this invention, methods of using the product are provided for altering the condition of in situ tissue of the same human donor by autoimplantation.

One method comprises placing an effective amount of the product, such as the completely solubilized solution or the partially solubilized suspension, e.g. as an injectable flowable mass, or formed into a putty like spreadable mass or finely divided distributable particles, at the in situ tissue site of the same donor, e.g. with the product being thereafter crosslinked in situ. Another method comprises placing the already crosslinked product as a shaped article or device at the in situ tissue site.

A particular method of using the completely solubilized product, especially where prepared with said selective index of refraction, concerns reshaping the cornea of an eye of the same human donor for correcting sight.

The method comprises applying a mold to the surface of the cornea of the eye to be reshaped, the mold having a concave surface of selective shape and size corresponding to an effective shape and size for the outer surface of the reshaped cornea for correcting the sight of the eye, injecting an effective amount of the product into the cornea, between a pair of adjacent lamellae in the region of the cornea outer surface, to form a mass between such lamellae causing the cornea outer surface to expand toward and into face to face contact with the mold concave surface, crosslinking the mass in situ to produce a shape retaining implant, and thereafter removing the mold.

Preferably, a vacuum is applied to the cornea during the injecting to facilitate the expanding of the cornea outer surface into contact with the mold concave surface. The crosslinking is effected for instance by irradiating the outer anterior portion of the cornea with ultraviolet (UV) rays. Also, the cornea is desirably flushed with nitrogen, argon or other inert gas during the crosslinking to remove oxygen from the irradiation site.

A particular method of using the product as an injectable flowable mass concerns reshaping the skin contour of the same human donor for substantially eliminating a dermal depression area. The method comprises injecting an effective amount of the optionally partially crosslinked product into the skin at the site of the dermal depression area to be reshaped, into the papillary dermic region, to form a mass in the intradermal tissue causing the skin outer surface to expand for substantially eliminating the depression area, and crosslinking the mass in situ to produce a shape retaining implant.

A particular method of using the completely solubilized product, especially where prepared with said selective index of refraction, concerns coating in situ tissue of an eye of the same human donor, by forming the product into an optionally partially crosslinked putty like spreadable mass, spreading an effective amount of the mass as a coating on the in situ tissue of the eye, e.g. as a thin, narrow coating across and into an incision as a sutureless tissue interconnector, and crosslinking the coating in situ to produce a shape retaining coating implant.

Another particular method of using the completely solubilized product, especially where prepared with said selective index of refraction, concerns replacing vitreous humor removed from the vitreous cavity of an eye of the same human donor, by optionally crosslinking the product sufficiently to provide an injectable flowable mass of gelatinous consistency corresponding to that of the vitreous humor, and injecting a replacement amount of the crosslinked mass into the vitreous cavity.

A further method of using the product in the form of a putty like spreadable mass concerns coating in situ tissue of the skin of the same human donor, by spreading an effective amount of the optionally partially crosslinked product as a coating on the in situ skin tissue, e.g. as a thin, narrow coating across and into an incision as a sutureless tissue interconnector, and crosslinking the coating in situ to produce a shape retaining coating implant.

An analogous method concerns using the product in the form of a putty like spreadable mass or finely divided distributable particles for coating in situ tissue at an internal surgical site of the same human donor, by spreading an effective amount of the optionally partially crosslinked spreadable mass as a coating and/or an interconnecting layer, or distributing an effective amount of the particles as a composite coating and/or composite interconnecting layer, on the in situ tissue at the internal surgical site, e.g. across and into a small incision in a limb blood vessel, and crosslinking the coating in situ to produce a shape retaining coating implant and/or interconnecting layer implant.

A further particular method of using the completely solubilized product, especially where prepared with said selective index of refraction, concerns reshaping the cornea of an eye of the same human donor for correcting sight, by forming the product into a mass of selective shape and size corresponding to an effective implant device for implanting in the cornea of the eye to be reshaped, between a pair of adjacent lamellae in the region of the cornea outer surface, for providing an effective convex shape for the outer surface of the reshaped cornea for correcting the sight of the eye, crosslinking the mass to produce a shape retaining implant device, and implanting the device between said pair of lamellae.

A still further method of using the completely solubilized product, especially where prepared with said selective index of refraction, concerns providing an intraocular implant lens for an eye of the same human donor, by forming the product into a mass of selective shape and size corresponding to an effective intraocular implant lens for the eye, crosslinking the mass, and upon surgically removing the natural eye lens from the eye, implanting the crosslinked intraocular implant lens in the eye.

A cognate method of using the completely solubilized product, especially where prepared with said selective index of refraction, concerns providing a contact lens for an eye of the same human donor, by forming the product into a mass of selective shape and size corresponding to an effective contact lens for the eye, crosslinking the mass to produce a shape retaining contact lens, and removably placing the contact lens in contact with the eye.

A still further method of using the completely solubilized, or partially solubilized, product concerns coating in situ tissue at an internal surgical site of the same human donor, by forming the product into a mass of selective shape and size corresponding to an effective implant device for coating and/or interconnecting the in situ tissue at the internal surgical site, crosslinking the mass to produce a shape retaining implant device, and implanting the device as a coating and/or interconnecting layer in contact with said tissue, e.g. in the form of a tubular shape retaining device, so as to enclose and interconnect severed ends of a limb blood vessel.

Considering the overall aspects of this invention, a basic method is also contemplated for altering the condition of in situ tissue of a human donor by autoimplantation, in which an effective amount of an autoimplantable collagenous substance is placed at the site of the in situ tissue of the same said human donor, said substance constituting a product produced by the process of chemically modifying, by any means, collagen from intact human tissue, which tissue has been obtained from the same said human donor alone, sufficiently to at least partially solubilize the collagen from the tissue, to form said autoimplantable collagenous substance as product, optionally crosslinked prior to being placed at said site or formed into a shape retaining implant device of selective shape and size and then placed at said site as a device implant.

Figure 1:
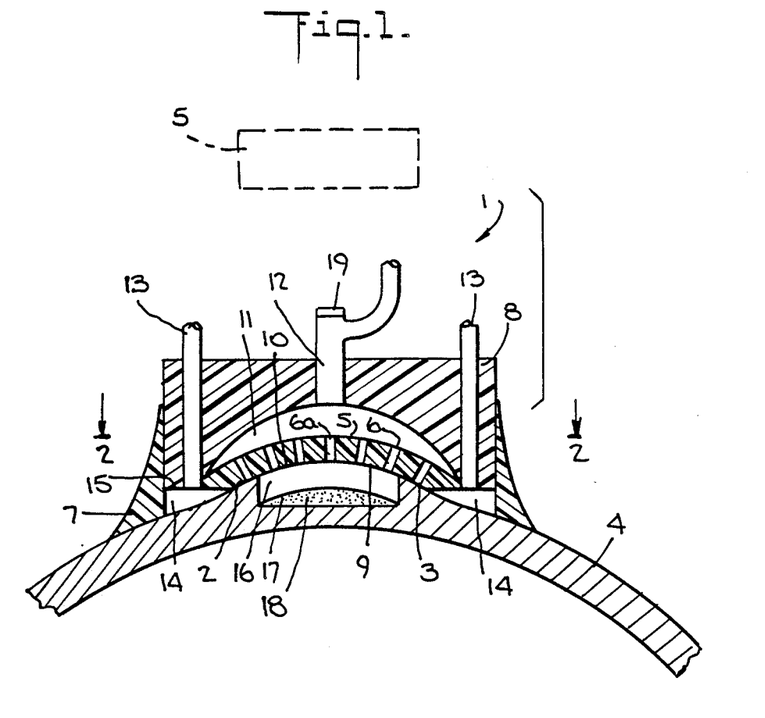
FIG. 1 is a schematic view of a mold device usable for carrying out the reshaping of the cornea of the eye of the human donor with an autoimplant crosslinked in situ, according to one embodiment of this invention.
Figure 2:
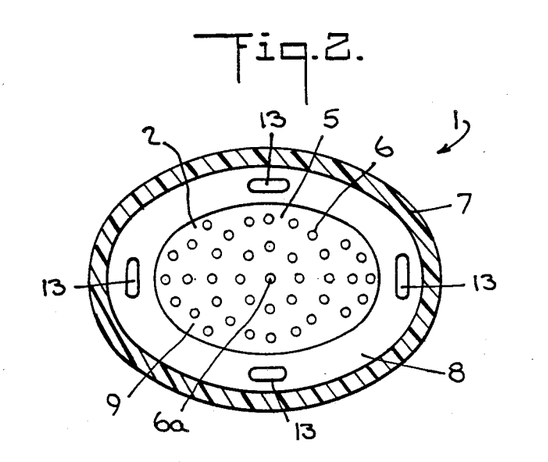
FIG. 2 is a sectional view of the device, taken along the line 2—2 of FIG. 1.

Referring to the drawings, FIGS. 1-2 show a mold 1 having a concave surface formation 2 corresponding to a predetermined convex shape for the outer surface 3 of the reshaped cornea 4 of the eye of the human donor, whose sight is to be corrected. Formation 2 includes a central forminous concave surface portion 5 of ultraviolet (UV) ray permeable plastic such as polymethylmethacrylate, containing a plurality of through pores 6, e.g. as a thin sieve or porous element, and a peripheral sealing rim portion 7 of soft pliable elastic material such as silicone plastic, e.g. as a skirt, depending from the main body 8 of mold 1. Body 8, like foraminous portion 5, is made of UV ray permeable plastic such as polymethylmethacrylate.

Mold 1 is applied to the cornea 4 such that foraminous portion 5 faces cornea outer surface 3 to define an expansion space 9 between the adjacent foraminous surface 10 and cornea outer surface 3, and such that rim portion 7 forms a substantially air tight seal with the adjacent cornea outer surface 3 surrounding expansion space 9.

Body 8 contains a distribution manifold 11, which flow communicates outwardly with the exterior of mold 1 via a central passage 12 and inwardly via pores 6 with space 9. Body 8 also contains a series of suitably circumferentially spaced apart peripheral passages 13, which flow communicate the peripheral circular conduit 14, defined between the underside of body 8 in the vicinity of the rim portion 7 and the area of cornea outer surface 3 surrounding expansion space 9, with the exterior of mold 1.

After the surgeon has predetermined the shape and volume of the desired corneal autoimplant to be used for correcting the sight of the concerned eye of the donor patient, an incision 16 is made in the cornea to form a pocket 17 of generally circular profile and extending substantially parallel to the cornea wall, between a pair of adjacent lamellae in the region of cornea outer surface 3. Then the collagen solution product is injected into pocket 17 in an effective amount to form a mass 18 between the adjacent lamellae corresponding to the predetermined volume of the desired implant.

This may be accomplished by inserting an injection needle through central passage 12, via an appropriate self-sealing perforatable membrane 19 located at the exterior portion of central passage 12, and in turn through a central pore 6a of foraminous portion 5, to incision 16 and pocket 17. As the injecting proceeds, cornea outer surface 3 is caused to expand toward and into the face to face contact with mold surface 10.

To aid in achieving expanding of cornea outer surface 3 in expansion space 9, and eventually full contact between cornea outer surface 3 and mold surface 10, a vacuum may be applied to cornea 4 via central passage 12, pores 6 and expansion space 9, of suction strength sufficient to draw the cornea outer surface region into contact with formation 2 as the injecting proceeds. To provide for a pressure differential in expansion space 9, compensating atmospheric air pressure may be applied via peripheral passages 13 to conduit 14.

Thereafter, mass 18 is crosslinked in situ by applying UV irradiation from a suitable source S, shown in phantom in FIG. 1, through mold 1, and foraminous portion 5, to the outer anterior portion of cornea 4 sufficiently to achieve conversion of mass 18 to a shape a retaining autoimplant. To aid in evacuating oxygen in the air from the irradiation site during the irradiation, nitrogen, argon or other inert gas may be fed via central passage 12 for distribution via manifold 11 and pores 6 to expansion space 9 for flushing cornea outer surface 3, such that the gas, e.g. nitrogen, flow exits via conduit 14 and peripheral passages 13.

Alternatively, the autoimplant may be made into a shaped insert in analogous manner, by determining the desired shape and size or volume of the implant, forming the collagen solution product into a mass of corresponding shape in a mold analogous to that shown in FIGS. 1-2, and UV irradiating the mass to form a shape retaining implant insert, whereupon the insert is implanted via a similar incision and pocket in the cornea of the eye of the donor.

In like manner, the skin contour of the donor may be reshaped for eliminating a dermal depression area, by injecting the collagen suspension product in an effective amount as a mass into the skin at the site of the dermal depression area to be reshaped, into the papillary dermic region, to form a mass in the intradermal tissue causing the skin outer surface to expand for eliminating the depression, such as a wrinkle line or scar tissue conformation, and then crosslinking the mass in situ as in the case of a cornea implant. Alternatively, the mass may be converted to a shape retaining autoimplant insert, as described above, and the insert placed at the skin depression area site via an incision providing an internal surgical site.

Other methods of using the product for altering the condition of in situ tissue of the same human donor by autoimplantation are analogously effected.

EXAMPLES

The following examples are set forth by way of illustration and not limitation of the present invention.

EXAMPLE 1

Complete Solubilization of Human Collagen

Human skin biopsy tissue (or human skin tissue obtained from reconstructive surgery, or the like), of the donor patient, is immediately frozen. Specimens of the frozen tissue are dissected to remove the attendant epidermal and subcutaneous layers, and the remaining dermal layer is sectioned.

(a) The sectioned frozen dermal layer is physically thoroughly pulverized in a physiological saline solution (0.9% NaCl in sterile water) as physiological solvent, by homogenization in a tissue homogenizer (conventional Polytron or Tekmar tissue mill) for about 30 seconds at room temperature (25° C.), sufficiently to produce a thoroughly pulverized white, fibrous cohesive mass of insoluble, highly crosslinked, native, telopeptide-containing collagenous tissue, as a solids phase. Noncollagenous components dissolve in the physiological solvent. Alternatively, the pulverizing may be carried out by conventional cryopulverization technique.

The solids phase is then separated by pipetting off the liquid. Homogenization (or cryopulverization) of the fibrous cohesive mass is repeated 6–10 times, each for a like period until the solution is clear and the fibrous mass is pure white and glistening, with subsequent separation from the physiological solvent liquid phase each time.

This purified material is finally separated from the attendant liquid, and then further thoroughly pulverized, by cryopulverization in the tissue mill (or alternatively by grinding in liquid nitrogen using a mortar and pestle) for an additional period of about 30 seconds. The resulting pulverized mass is recovered as a tissue powder of the now noncollagenous protein contaminate-free, insoluble fibrous, highly crosslinked, native, telopeptide-containing collagenous substance.

(b) To remove lipid contaminants, the tissue powder is mixed with 20 volumes of 95–98% ethanol, the resultant organic solvent extracted powder is recovered by centrifugation, and the residual ethanol removed by vacuum drying. Alternatively, the residual ethanol is removed by washing three times with 20 volumes of demineralized water.

The resulting ethanol-free tissue powder is then placed in 20–50 times its volume of physiological aqueous 0.9M NaCl solution (or buffered saline), to form an aqueous liquid suspension.

All of the above procedures are carried out in a laminar flow, Class 100 hood to prevent contamination.

(c) The suspension is adjusted to moderately basic pH, i.e. pH 8.5, by adding 1–4N NaOH, and then reacted at room temperature (25° C.) for about 30 minutes with succinic anhydride as amine reactive modifying agent, which is slowly added in portions with agitation to the suspension. The pH is continuously maintained at 8.5 by adding further NaOH as needed. As the reaction proceeds, the fibrous collagenous substance is chemically modified, and the suspension becomes clear and viscous due to the solubilization of the collagen. The reaction is terminated by increasing the pH to 12.0, with 5N NaOH.

The completely solubilized material in the aqueous liquid is a transparent, viscous telopeptide-containing collagen "solution" product, e.g. usable as an ophthalmic autoimplant material. The reaction can be stopped at any point to limit the degree of chemical modification and solubilization of the collagenous substance.

The solubilized product constitutes chemically modified, crosslinkable, telopeptide-containing, naturally crosslinked, collagen, in which the individual helical strands of the triple helix molecules remain in interconnected side by side helical disposition along the corresponding collagen polypeptide backbone, with the terminal amino group-containing site of each given strand still linked to its adjacent non-helical telopeptide end moiety, and with the terminal carboxylic acid group-containing site of the same strand still linked to its adjacent non-helical telopeptide end moiety.

Thus, all three helical strands of one tropocollagen molecule remain linked at their ends to their respective telopeptide moieties, telopeptide moieties remain crosslinked to adjacent tropocollagen molecules, and adjacent helical strands remain crosslinked to each other along their central regions, and to telopeptide regions of adjacent tropocollagen molecules, to retain the original polypeptide backbone arrangement and to retain some order of the original intermolecular configuration. However, these strands now contain acylated (succinylated) amino groups which render the collagen soluble at neutral to basic pH, while still preserving the integrity of the intermolecular arrangement.

It will be understood that these individual chemically modified tropocollagen molecules, consequent their solubilization, are no longer in packed staggered arrangement in fibrils of fiber bundles as in the starting tissue, but rather constitute substantially intact separate units, which are completely dissolved in the reaction medium where complete solubilization is carried out. If partial solubilization is carried out, the suspension contains a mixture of intact separate units and various degrees of fiber units sized in dependence upon the extent of solubilization, which are suspended or dispersed in the reaction medium as fine particle material.

Comparable results are obtainable using glutaric anhydride, monophenyl terephthalate, ethyl benzoate, alpha-naphthoic acid ethyl ester, succinic acid chloride, 4-amino-naphthalene sulfonic acid, 4,4'-biphenyl disulfonyl chloride, or benzene sulfonyl chloride, as the chemical modifying agent.

(d) After the reaction is stopped, the completely solubilized collagenous substance is recovered by precipitation by reducing the pH of the aqueous liquid reaction mixture to about 4.3 with 1N HCl. The precipitate is purified by washing 3–5 times in sterile acidified water having a pH 4.3 to remove unreacted modifier constituents, and then dissolved in aqueous buffered physiological neutral pH saline solution (0.9M NaCl) to form a transparent thick liquid collagen solution product.

(e) This solution product may be injected as a cornea autoimplant, and crosslinked in situ by UV irradiation. Alternatively, it may be formed into a mass of shape and size corresponding to a cornea autoimplant and crosslinked to form a thin, pliable transparent film for corneal autoimplantation.

EXAMPLE 2

Partial Solubilization of Human Collagen

The procedure of Example 1, part (c), is repeated, except that the reaction is stopped after the collagenous substance is only partially solubilized. The product is a cloudy, viscous suspension of partially solubilized and partially insoluble collagenous substance in the aqueous liquid reaction mixture. It is insoluble in aqueous physiological saline solution, and constitutes the same type telopeptide-containing, crosslinkable product as described in Example 1, part (c).

Unreacted chemical modifier constituents are removed by washing with neutral buffered aqueous solution. A precipitate is formed, recovered by centrifugation, and mixed with neutral buffered physiological saline solution to form a collagen suspension, constituting a substantially homogenous solution which contains suspended material having acylated amine groups (2–10% collagen).

The suspension product passes through a 27 gauge needle and forms a white precipitate when injected into physiological buffer solution.

The suspended product is injected as a skin autoimplant to eliminate a dermal depression area, i.e. a wrinkle line, and crosslinked in situ by UV irradiation. The product is alternatively formed into a mass of shape and size corresponding to a skin depression, crosslinked to form a shape retaining implant device as a thin, pliable film, and autoimplanted in the skin.

EXAMPLE 3

Index of Refraction Modified Collagen

The procedure of Example 1 is repeated, except that the reaction is carried out with aniline-2-sulfonic acid as amine reactive chemical modifying agent, or by sequential reaction with aniline-2-sulfonic acid followed by succinic anhydride, to provide the completely solubilized telopeptide-containing collagenous substance in the form of a clear and transparent liquid collagen solution. This product constitutes the same type telopeptide-containing, crosslinkable product as described in Example 1, part (c), yet has a selective specific high index of refraction. It can be used as in Example 1 as a cornea autoimplant material for correcting sight (index of refraction nD of aniline-2-sulfonic acid=1.586).

Comparable results are obtained using 3-nitrobenzene-sulfonic acid (nD=1.550); 2-formylbenzene-sulfonic acid (nD=1.544); 1,2,4,5-benzene tetracarboxylic acid dianhydride, and 1,3-benzene disufonic acid, as the amine reactive high refractive index imparting chemical modifying agent.

EXAMPLE 4

Complete Solubilization of Human Collagen (a) A section of human dermis, approximately 1 cm×1 cm, was dissected from a specimen of human tissue obtained from an adult donor during reconstructive surgery. The undried section weighed about 1.25 grams and was sliced into small strips using a scalpel, and placed in 20 ml of aqueous 0.9% NaCl solution. The tissue was then homogenized at room temperature (25° C.) in a mill (Technical Instruments MicroMill). Homogenization was performed in two separate aliquots. Grinding for 30 seconds was repeated ten times for each aliquot. After each 30 second grinding run, the mill was opened, the fluid removed with a 10 cc pipette, and an equal volume of fresh aqueous 0.9% NaCl solution added. This procedure allowed the removal of extraneous noncollagenous protein contaminate fluids and resulted in the formation of a white, glistening, stringy mass of collagenous tissue. This mass was cohesive and could not be further homogenized in the mill. The fibrous structure was then cut into small pieces using surgical scissors.

(b) To remove lipid contaminants, the resulting mass may be mixed with 20 volumes of 95–98% ethanol, the resultant organic solvent extracted mass recovered by centrifugation, and the residual ethanol removed by vacuum drying. Alternatively, the residual ethanol may be moved from the centrifuged mass after the lipid extraction step by washing three times with 20 volumes of deionized water.

(c) The purified pieces were placed in 10 ml of fresh aqueous 0.9% NaCl solution and aliquoted into the mill. The pH was adjusted to 9.0 using 5N NaOH, and about 120 mg of finely powdered succinic anhydride were added. The resulting suspension was then ground for 60 second intervals at room temperature. Between intervals the pH was readjusted to 8.5 using 1N NaOH, until the pH of the ground material appeared to stabilize at about 7.0.

Then a second 120 mg succinic anhydride amount was added to the suspension and the homogenization continued with pH adjustment to 8.5 using 1N NaOH, following 60 second pulverization runs. The pH adjustments were stopped when the fibrous mass was converted to a transparent gelatinous mass. The pH was then raised to 12 using 5N NaOH to stop the reaction. The solubilized product constitutes the same type telopeptide-containing, crosslinkable collagen as described in Example 1, part (c).

(d) After 2 minutes the pH was reduced to 4.2 using 1N HCl to precipitate the solubilized collagen in a white to gray fibrous mass. The precipitate was washed four times with pH 4.2 deionized water, and centrifuged at approximately 10,000×g. to remove excess fluid. The resulting mass weighed 43 mg and was reconstituted in a balanced salt solution (Akorn) at about 0.25% solids and a pH of 7.2.

This balanced salt solution (Akorn) contains per ml: 0.64% sodium chloride, 0.075% potassium chloride, 0.048% calcium chloride, 0.03% magnesium chloride, 0.39% sodium acetate, 0.17% sodium citrate, and sufficient sodium hydroxide and/or hydrochloric acid to adjust the pH of the resultant product, plus sufficient water to provide a product form suitable for injection.

The diluted collagen solution was then filtered through a 0.45 μ Gelman syringe filter to remove physically any attendant particulate matter. Preferably, the solution is filtered through a 0.2 μ filter, which is able to filter finer particles (such as microorganisms) to achieve an acceptable degree of sterilization.

The resulting filtered solution was placed in a sterile centrifuge tube and the pH adjusted to 4.2 to reprecipitate the collagen. The material was centrifuged at approximately 10,000×g. to recover the precipitate and the precipitate adjusted to pH 7.2 by dropwise addition of 1N NaOH. The resulting material at approximately 2–3% solids (collagen) was a transparent, slightly hazy, viscous and viscoelastic solution amounting to about 2 cc.

(e) This process produced total solubilization of the telopeptide collagen of the human dermis. The solution product may be used to reshape the cornea of the same donor per the procedure described in connection with the mold of FIGS. 1-2.

EXAMPLE 5

Partial Solubilization of Human Collagen

For preparing injectable collagen to correct dermal defects it is necessary to limit the solubilization process so as to obtain a more fibrous, robust product. Thus, preparation of the human collagen for dermal injection employs only partial solubilization of the telopeptide collagen.

The procedure of Example 4 was repeated, again using the mill to disrupt and pulverize the tissue mass to provide a white, stringy mass of collagenous tissue. Solubilization was effected in the mill by treatment with succinic anhydride, but the reaction was stopped when the fibrous mass appeared as a heterogenous mixture of larger fibrous pieces and fine powdery particles in a gelatinous mass. Only one succinic anhydride addition was needed and six pH adjustments were made. The product constitutes the same type telopeptide-containing, crosslinkable collagen as described in Example 2.

The mixture was centrifuged at about 10,000× g. for 20 minutes to separate the large particles from the fine, powdery material in the gelatinous mass. The gelatinous mass free of the large particles could be injected through a 25 gauge needle. When injected into balanced salt solution (Akorn) [see Example 4], the fine particles aggregated into a fibrous mass which can be used as an autoimplant to correct a dermal defect.

The product is combined with glycerol to retard collagen fibril formation and stabilize the collagen preparation, and then used by injection into the papillary dermic region to form a mass in the intradermal tissue of the skin of the donor to eliminate a local site of dermal depression. This is followed by UV irradiation in situ to achieve crosslinking. Alternatively, the crosslinking may be effected by gamma irradiation, chemical curing with glutaraldehyde, and combinations of dehydration and UV irradiation.

EXAMPLE 6

Index of Refraction Modified Collagen

The procedure of Example 4 was repeated, except that the reaction was effected using aniline-2-sulfonic acid instead of succinic anhydride to provide a completely solubilized telopeptide collagen having the same high index of refraction as the product described in Example 3. The solution product is used as a corneal autoimplant material as noted above.

EXAMPLE 7

Collagen Film Preparation

One ml of completely solubilized telopeptide-containing collagen, prepared according to the procedure of Example 4, was placed in a concave microscope slide which served as a simple concave mold. The sample was positioned 9.5 cm below a Gelman Model 51938 UV lamp and both were placed in a sealed polyethylene bag. Oxygen was evacuated by flushing with nitrogen for 15 minutes. The UV lamp was activated and flushing continued throughout the UV irradiation. The light was illuminated at 253.7 nm for 20 minutes at room temperature. The slide was placed on moist paper towels to provide humidity and prevent dehydration of the solution. The irradiation crosslinked the collagen into a thin, flexible concave film that was transparent and slightly yellow.

An alternative method of evacuating the oxygen is to place a Gaspak (Becton Dickinson & Co., BBL Microbiology system containing sodium borohydride and sodium carbonate) in the closed chamber for 15 minutes.

Comparable results are obtained using alternative methods of curing the collagen, including gamma irradiation crosslinking, chemical crosslinking with glutaraldehyde as tanning or curing agent, and combinations of dehydration and UV irradiation for crosslinking.

EXAMPLE 8

Solubilization With Esterification

Example 4 is repeated, except that in part (d), before the centrifuged mass is reconstituted in a balanced salt solution, it is subjected to vacuum drying to remove attendant water, and then combined with 20 ml of dehydrated ethanol, as carboxylic acid reactive modifying agent, which has been acidified with 0.1N HCl to a pH of not more than about 3.2, and reacted at room temperature (25° C.) for about 30 minutes with agitation in a closed vessel to preserve the nonaqueous reaction mixture. The ethanol is present in large excess over the quantity needed to esterify the available carboxylic acid groups of the amino group acylated (succinylated) telopeptide-containing collagen prepared in part (c).

After the ethylation, the collagen is recovered by vacuum drying. Alternatively, the reaction mixture is mixed with an equal volume of ethyl ether and extracted with deionized water. In either case, the resulting precipitate is washed four times with pH 4.2 deionized water, and centrifuged at approximately 10,000×g. to remove excess fluid. The resulting mass is then reconstituted in balanced salt solution (Akorn) [see Example 4] at about 0.25% solids and a pH of 7.2, and the remainder of Example 4, part (d) is then carried out.

In the amplified procedure of this example, the carboxyl groups of the collagen are modified by esterification reaction with the ethanol to change the charge extant on the collagen molecules and provide a collagenous molecular structure more soluble at neutral pH in aqueous medium.

The three helical strands of the tropocollagen molecule remain linked to their respective telopeptide moieties to retain the original polypeptide backbone arrangement, yet now contain both acylated (succinylated) amine groups and esterified (ethylated) carboxyl groups (carboxylic acid ethyl esters).

The product is used in the same way as that of Example 4.

EXAMPLE 9

Solubilization By Esterification Alone

Example 4, parts (a) and (b) are repeated, and the purified pieces of pulverized material are dried by vacuum drying to remove attendant water (or freeze dried), and then combined in the tissue mill with 40 ml of dehydrated ethanol as carboxylic acid reactive modifying agent, which has been acidified with 0.1N HCl to a pH of not more than about 3.2. Upon closing and operating the mill, the suspension is reacted at room temperature (25° C.) for about 30 minutes. During this time, the nonaqueous reaction mixture is preserved by keeping the mill closed. The ethanol is present in large excess over the quantity needed to esterify the available carboxylic acid groups of the telopeptide-containing collagen.

After the ethylation, the collagen is recovered and worked up in the same manner as in Example 8.

In this procedure, the carboxyl groups of the collagen are modified by esterification reaction with the ethanol to change the charge extant on the collagen molecules and provide a collagenous molecular structure which is soluble at neutral to basic pH in aqueous medium.

The solubilized product constitutes chemically modified, crosslinkable, telopeptide-containing collagen, which differs from that of the product of Example 1 only in that the strands of the triple helix molecule contain esterified (ethylated) carboxyl groups (carboxylic acid ethyl esters) instead of acylated (succinylated) amine groups, yet which analogously render the collagen soluble at neutral to basic pH.

The product is used in the same way as that of Example 4.

Comparable results are obtainable using dehydrated methanol, phenol (in acetone) and alpha-naphthol (in DMF), acidified with 0.1N HCl. Alternatively, in each case the reaction can be stopped before complete solubilization, and the desired product recovered, purified and worked up in corresponding manner to form a product analogous to that of Examples 2 and 5.

In connection with the above specific examples, the following product preparations may be used:

a. injectable solution concentration, about 1 to 5% collagen content, b. preformed ophthalmic implant (device), about 2 to 10% collagen content, c. tissue augmentation implant, about 2 to 10% collagen content.

It will be appreciated that the foregoing specification and accompanying drawings are set forth by way of illustration and not limitation of the present invention, and that various modifications and changes may be made therein without departing from the spirit and scope of the present invention which is to be limited solely by the scope of the appended claims.

What is claimed is:

1. Method for altering the condition of in situ tissue of a sole human donor by autoimplantation, comprising placing an effective amount of an autoimplantable, crosslinkable, telopeptide-containing collagen at the site of the in situ tissue of said donor, said collagen constituting a product produced by the process of reacting a solids phase extract from tissue, which tissue has been obtained from the same said donor and said extract obtained by comminuting said tissue and treating to remove soluble proteins, with an amine reactive acylating agent or a carboxylic acid reactive esterifying agent.

2. Method of claim 1 wherein said collagen is thereafter crosslinked in situ.

3. Method for altering the condition of in situ tissue of a sole human donor by autoimplantation, comprising placing an effective amount of an autoimplantable collagen at the site of the in situ tissue of said donor, said collagen constituting a product produced by the process of chemically modifying telopeptide-containing collagen obtained from human tissue by comminuting said tissue and treating to remove soluble proteins, which tissue has been obtained from the same said donor, sufficiently to at least partially solubilized the collagen from the comminuted tissue.

4. Method of claim 3 wherein said autoimplantable collagen is crosslinked before being placed at the site.

5. Method of claim 1 used for reshaping the cornea of an eye of the same human donor for correcting sight, comprising:

applying a mold to the surface of the cornea of the eye to be reshaped, the mold having a concave surface of selective shape and size corresponding to an effective shape and size for the outer surface of the reshaped cornea for correcting the sight of the eye, injecting an effective amount of said collagen in injectable solution form into the cornea, between a pair of adjacent lamellae in the region of the cornea outer surface, to form a mass between such lamellae causing the cornea outer surface to expand toward and into the face to face contact with the mold concave surface, crosslinking the mass or allowing the mass to autopolymerize in situ to produce a shape retaining implant, and thereafter removing the mold from the cornea.

6. Method of claim 1 used for replacing vitreous humor removed from the vitreous cavity of an eye of the same human donor, comprising:

crosslinking said collagen in solution form sufficiently to provide an injectable flowable mass of gelatinous consistency corresponding substantially to that of the vitreous humor of the eye of the same donor, and injecting a replacement amount of the crosslinked mass into the vitreous cavity of said eye.

7. Method of claim 1 used for reshaping the skin contour of the same human donor for substantially eliminating a dermal depression area, comprising:

injecting an effective amount of said collagen in injectable form into the skin of the same donor at the site of the dermal depression area to be reshaped, primarily into the papillary dermic region, to form a fibrous, cohesive mass in the intradermal tissue causing the skin outer surface to expand for substantially eliminating the depression area, and crosslinking the mass or allowing the mass to autopolymerize in situ to produce a shape retaining implant.

8. Method for altering the condition of in situ tissue of a sole human donor, comprising placing an effective amount of an autoimplantable, telopeptide-containing collagen at the site of the in situ tissue of said donor, said collagen constituting a product produced by reacting a solids phase extract from tissue obtained from the same said donor, said extract obtained by comminuting said tissue and treating to remove soluble proteins, with an amine reactive acylating agent or a carboxylic acid reactive esterifying agent.

9. Method of claim 8 wherein said collagen is crosslinkable and is crosslinked before being placed at the site.

10. Method of claim 8 wherein the said collagen having acylated amine groups or esterified carboxyl groups, is purified and formed into a mass of selective shape and size, and thereafter crosslinked prior to being placed at said site.

11. Method of claim 3 wherein said autoimplantable collagen is crosslinked after being placed at the site.

* * * * *